(12) United States Patent
Mason et al.

(10) Patent No.: US 7,059,329 B2
(45) Date of Patent: *Jun. 13, 2006

(54) KNEE BRACE PROVIDING DYNAMIC TRACKING OF THE PATELLO-FEMORAL JOINT

(75) Inventors: Jeffrey T. Mason, Escondido, CA (US); James M. Fout, Oceanside, CA (US); Raymond S. Veeck, San Diego, CA (US)

(73) Assignee: Breg, Inc., Vista, CA (US)

( * ) Notice: Subject to any disclaimer, the term of this patent is extended or adjusted under 35 U.S.C. 154(b) by 210 days.

This patent is subject to a terminal disclaimer.

(21) Appl. No.: 10/728,736

(22) Filed: Dec. 5, 2003

(65) Prior Publication Data

US 2004/0167452 A1 Aug. 26, 2004

Related U.S. Application Data

(63) Continuation-in-part of application No. 10/420,344, filed on Apr. 22, 2003, which is a continuation-in-part of application No. 09/669,061, filed on Sep. 22, 2000, now Pat. No. 6,551,264.

(51) Int. Cl.
*A61C 5/14* (2006.01)

(52) U.S. Cl. .................................... 128/861; 433/89
(58) Field of Classification Search ............ 602/41–44, 602/26, 16, 60, 61, 23, 5, 63; 128/882
See application file for complete search history.

(56) References Cited

U.S. PATENT DOCUMENTS

| | | | |
|---|---|---|---|
| 3,581,741 A | 6/1971 | Rosman | 128/80 |
| 4,201,203 A | 5/1980 | Applegate | 128/80 |
| 4,296,744 A | 10/1981 | Palumbo | 128/80 |
| 4,370,978 A | 2/1983 | Palumbo | 128/80 |
| 4,423,720 A | 1/1984 | Meier et al. | 128/80 |
| 4,425,912 A | 1/1984 | Harper | 128/80 |
| 4,445,505 A | 5/1984 | Labour et al. | 128/80 |
| 4,466,428 A | 8/1984 | McCoy | 128/80 |
| 4,506,661 A | 3/1985 | Foster | 128/80 |
| 4,554,913 A | 11/1985 | Womack et al. | 128/80 |
| 4,572,170 A | 2/1986 | Cronk et al. | 128/80 |
| 4,607,628 A | 8/1986 | Dashefsky | 128/80 |
| 4,633,867 A | 1/1987 | Kausek et al. | 128/80 |
| 4,681,097 A | 7/1987 | Pansiera | 128/77 |
| 4,854,308 A | 8/1989 | Drillo | 128/80 |
| 4,872,448 A | 10/1989 | Johnson, Jr. | 128/80 |
| 4,991,571 A | 2/1991 | Kausek | 128/80 C |
| 5,024,216 A | 6/1991 | Shiono | 128/80 |
| 5,277,697 A | 1/1994 | France et al. | 602/16 |

(Continued)

*Primary Examiner*—Kim Lewis
(74) *Attorney, Agent, or Firm*—Rodney F. Brown

(57) ABSTRACT

A knee brace is provided having upper and lower arms and a hinge assembly positionable about the knee to one side of the patella. The hinge assembly has a hinge pivot and a tension strap lever. The upper and lower arms and tension strap lever are each rotatable about the hinge pivot. A compression member is positioned in engagement with the knee on the opposite side of the patella from the hinge assembly and a tension strap engages the compression member and is connected to the tension strap lever. The tension strap applies a tension force to the compression member which increases when the upper and lower arms and tension strap lever rotationally transition from a flexion position to an extension position and decreases when the upper and lower arms and tension strap lever rotationally transition from the extension position to the flexion position.

9 Claims, 7 Drawing Sheets

U.S. PATENT DOCUMENTS

| | | | |
|---|---|---|---|
| 5,288,287 A | 2/1994 | Castillo et al. | 602/16 |
| 5,458,565 A | 10/1995 | Tillinghast, III et al. | 602/26 |
| 5,554,105 A | 9/1996 | Taylor | 602/26 |
| 5,556,374 A | 9/1996 | Grace et al. | 602/26 |
| 5,613,943 A | 3/1997 | Palumbo | 602/62 |
| 5,759,167 A | 6/1998 | Shields, Jr. et al. | 602/26 |
| 5,772,618 A | 6/1998 | Mason et al. | 602/16 |
| 5,782,780 A | 7/1998 | Mason et al. | 602/6 |
| 5,797,864 A | 8/1998 | Taylor | 602/26 |
| 5,807,294 A | 9/1998 | Cawley et al. | 602/26 |
| 5,807,298 A | 9/1998 | Palumbo | 602/62 |
| 5,857,988 A | 1/1999 | Shirley | 602/26 |
| 5,865,776 A | 2/1999 | Springs | 602/26 |
| 5,873,848 A | 2/1999 | Fulkerson | 602/62 |
| RE37,297 E | 7/2001 | Smith, III | 602/26 |
| 6,551,264 B1 * | 4/2003 | Cawley et al. | 602/16 |
| 2003/0176823 A1 | 9/2003 | Mason | |
| 2003/0176824 A1 | 9/2003 | Mason | |

* cited by examiner

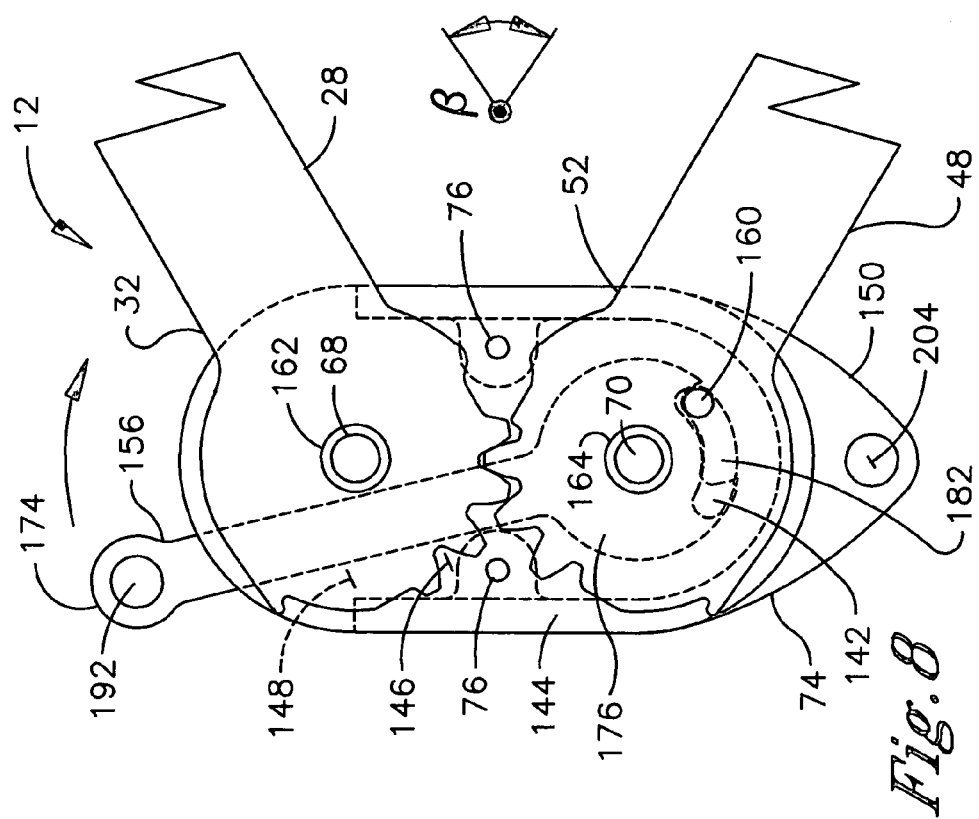
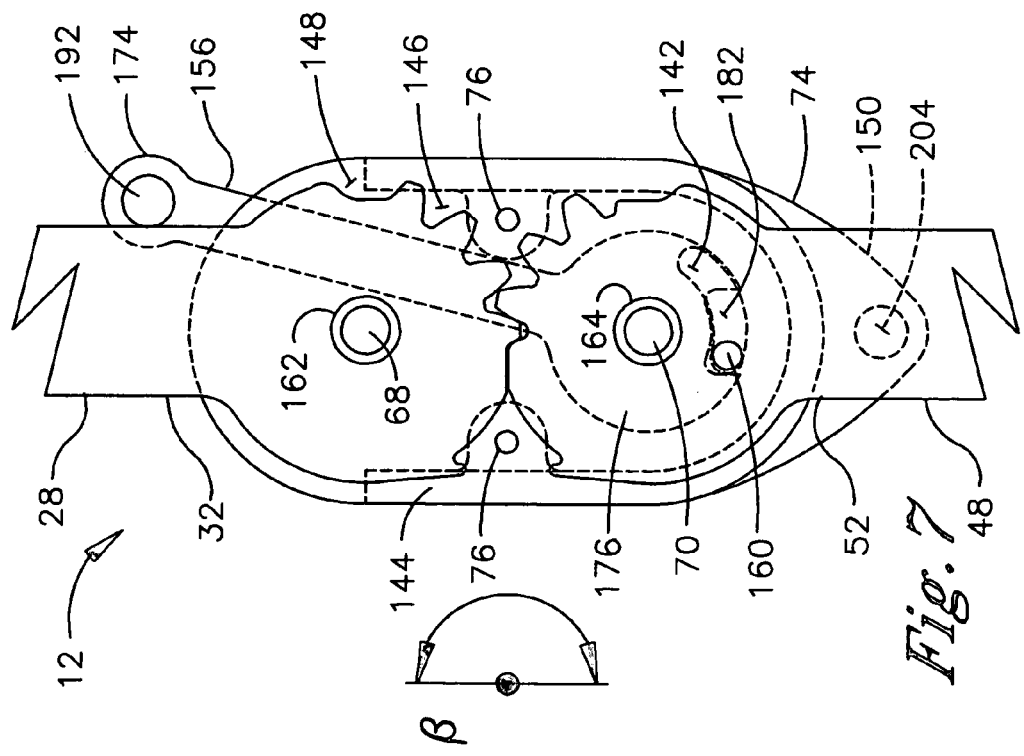

KNEE BRACE PROVIDING DYNAMIC TRACKING OF THE PATELLO-FEMORAL JOINT

This a continuation-in-part application of Ser. No. 10/420,344 filed on Apr. 22, 2003, which is a continuation-in-part application of Ser. No. 09/669,061 filed on Sep. 22, 2000 and issued on Apr. 22, 2003, as U.S. Pat. No. 6,551,264.

TECHNICAL FIELD

The present invention relates generally to knee braces, and more particularly to a knee brace which causes the patella to properly track the trochlear groove during movement of the knee joint.

BACKGROUND OF THE INVENTION

The knee joint includes a patello-femoral joint which is an articulation between the patella and femur. The patello-femoral joint consists of an articular surface on the posterior of the patella and a corresponding articular surface on the anterior of the head of the femur which is termed the trochlea. The posterior of the patella is contoured as a ridge, while the trochlea is contoured as a groove which is dimensioned to receive the patellar ridge in a complementary manner. Proper dynamic function of the patello-femoral joint requires that the patellar ridge accurately track the underlying trochlear groove when the knee joint is moved through flexion or extension. The anatomy and function of the patello-femoral joint are well known and described in detail in Ficat, R. P. et al., *Disorders of the Patello-femoral Joint*, Williams & Wilkins, 1977.

Functional disorders of the patello-femoral joint frequently relate to improper dynamics. Less severe forms of patello-femoral joint disorder cause pain in the joint, but do not exhibit errors in patellar tracking of the trochlear groove. In more severe forms of patello-femoral joint disorder, patellar tracking errors are evident in addition to joint pain, but there is no subluxation or dislocation of the joint. In still more severe forms of patello-femoral joint disorder, patellar tracking errors result in subluxation or dislocation of the joint. Recurrent subluxation of the patello-femoral joint is a particular disorder whereby the patella deviates transiently and typically rapidly from its normal axis of movement due to patellar tracking errors during movement of the knee joint. Slight deviations of the patella from its normal axis of movement are termed minor subluxation and may not produce any clinically apparent relocation of the patella. Minor subluxation is often the result of a functional imbalance in the knee joint. Significant deviations of patellar movement which approach dislocation are termed major subluxation. Major subluxation can be brought on by strenuous activity although it often occurs even in the absence of such activity. Recurrent patellar subluxation, both major and minor, is a relatively frequent condition among women generally and particularly among women athletes.

Most instances of subluxation or dislocation of the patella due to patellar tracking errors are in the lateral direction because biomechanical forces typically bias the patella laterally when the knee joint is load-bearing. In addition, subluxation or dislocation of the patella due to patellar tracking errors has the greatest risk of occurring when the knee joint is approaching extension. When the knee joint ranges between about 30° of full extension and full extension, the trochlear groove becomes relatively small and shallow which is conducive to subluxation or dislocation. Functional disorders of the patello-femoral joint are highly undesirable because such disorders may ultimately lead to cartilage damage and arthritis of the knee joint. Therefore, a recognized need exists for effective preventative or remedial treatment of patello-femoral joint disorders.

It is an object of the present invention to provide a knee brace which prevents or remediates functional disorders of the patello-femoral joint including recurrent patellar subluxation or dislocation. More particularly, it is an object of the present invention to provide a knee brace which reduces the risk of patellar tracking errors by providing the knee joint with a patellar tracking guide. It is a specific object of the present invention to provide a knee brace which applies a patellar tracking guide to the head of the femur laterally or medially adjacent to the patella to reduce the risk of recurrent lateral or medial patellar subluxation or dislocation. It is a further object of the present invention to provide a knee brace having a patellar tracking guide which dynamically tensions when the knee joint approaches the extension position for maximum effect and dynamically relaxes when the knee joint approaches the flexion position to minimize interference with the function of the knee joint. It is still a further object of the present invention to provide a knee brace having a patellar tracking guide which is dynamically positioned more proximal to the patella when the knee joint approaches the extension position for maximum effect and is dynamically positioned more distal to the patella when the knee joint approaches the flexion position to minimize interference with the function of the knee joint. These objects and others are accomplished in accordance with the invention described hereafter.

SUMMARY OF THE INVENTION

The present invention is a brace mountable about a knee joint having a femoral head and patella. The brace comprises first upper and lower arms positionable about the knee joint and a first hinge assembly positioned between the first upper and lower arms and positionable at the knee joint to one side of the patella. The first hinge assembly comprises a lower end of the first upper arm, an upper end of the first lower arm, a tension strap lever including a tension strap connection point and a hinge pivot rotationally engaging the lower and upper ends of the first upper and lower arms, respectively, and the tension strap lever. The first upper and lower arms and the tension strap lever are rotatable about the hinge pivot to transition between a flexion position and an extension position. The brace may further comprise second upper and lower arms and a second hinge assembly positioned at the knee joint to the opposite side of the patella from the first arms and first hinge assembly. Upper and lower stiffened cuffs are provided to retain the upper and lower arms in relation to the knee joint.

A compression member is positioned at the femoral head adjacent to the patella on the opposite side of the patella from the first hinge assembly. In accordance with one embodiment, the compression member comprises a tracking guide engaging the knee joint and a compression plate in overlying engagement with the tracking guide. The compression plate is formed from a more rigid material than the relatively pliant tracking guide. A tension strap is connected to the tension strap lever at the tension strap connection point and additionally engages the compression member.

When the first upper and lower arms and tension strap lever rotationally transition from the flexion position to the extension position, the tension strap connection point is posteriorly displaced relative to the hinge pivot more distal from the patella, thereby increasing the tension force applied to the compression member. Conversely, when the first upper and lower arms and tension strap lever rotationally transition from the extension position to the flexion position, the tension strap connection point is anteriorly displaced relative to the hinge pivot more proximal to the patella, thereby decreasing the tension force applied to the compression member. The brace is further provided with a counterbalance connector connected to the tension strap.

The present brace enables a method for maintaining proper tracking of the patella relative to the femoral head during range of motion movement of the knee joint. The method is initiated by placing the compression member in engagement with the knee joint at a location on the femoral head adjacent to the patella. The compression member is aligned with a desired dynamic patellar track. Range of motion movement is then performed on the knee joint by moving the knee joint from a flexion position to an extension position or from an extension position to a flexion position while applying a tension force to the compression member by the tension strap. The tension force increases when the tension strap connection point is posteriorly displaced away from the patella by the first hinge assembly as the knee joint approaches the extension position. Conversely, the tension force decreases when the tension strap connection is anteriorly displaced toward from the patella by the first hinge assembly as the knee joint approaches the flexion position. As such, the compression member presses against the femoral head with a variable tension force which enables the compression member to conform the patella to the desired dynamic patellar track during movement of the knee joint.

The present invention will be further understood from the drawings and the following detailed description.

BRIEF DESCRIPTION OF THE DRAWINGS

FIG. 7 is an operational medial view of the hinge assembly of FIG. 5 in the extension position.

FIG. 8 is an operational medial view of the hinge assembly of FIG. 5 in the flexion position.

DESCRIPTION OF PREFERRED EMBODIMENTS

Figure 1:
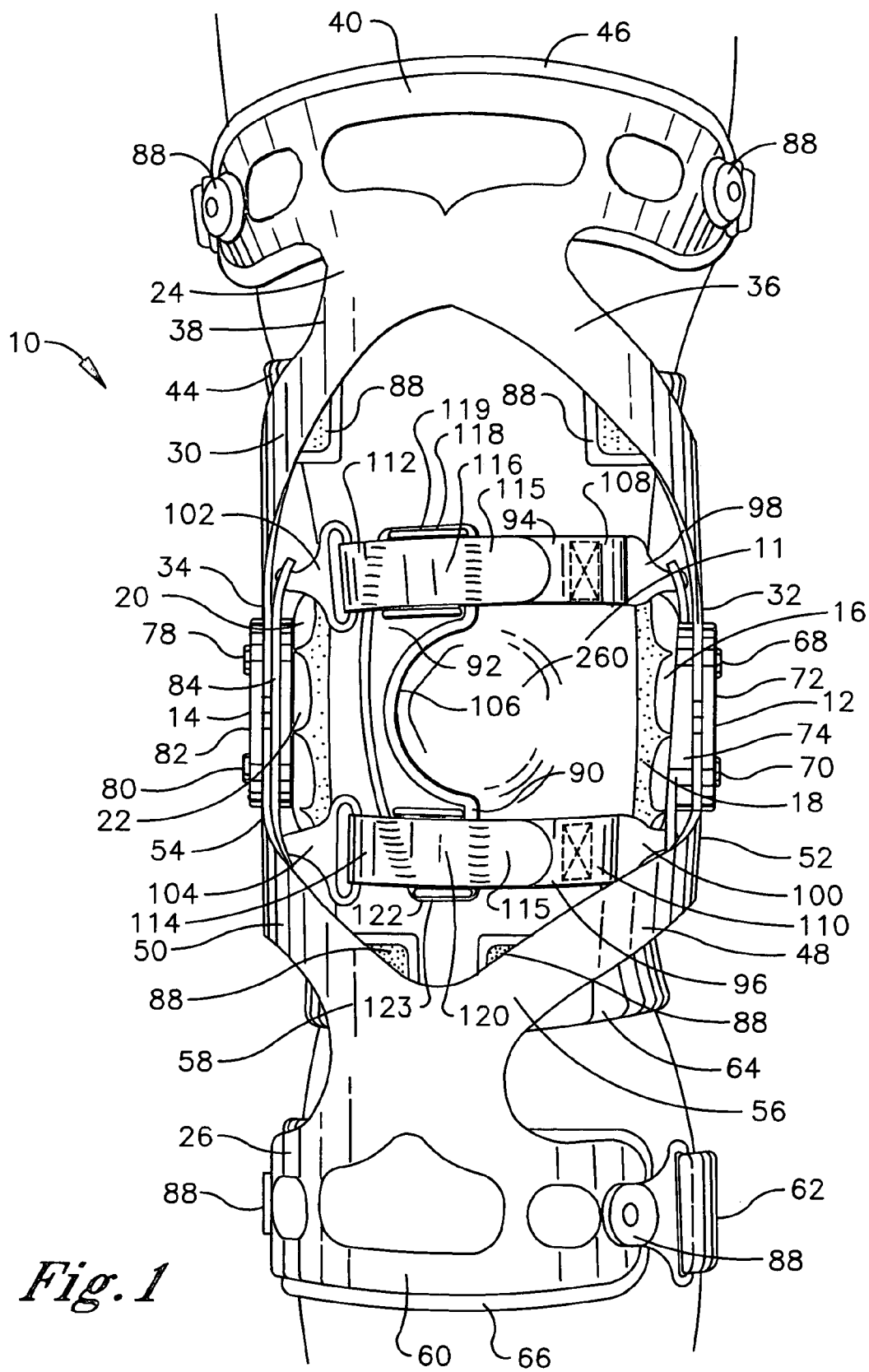
FIG. 1 is an anterior view of a knee brace of the present invention operatively positioned about the knee joint of a user with the knee joint in the extension position.
Figure 2:
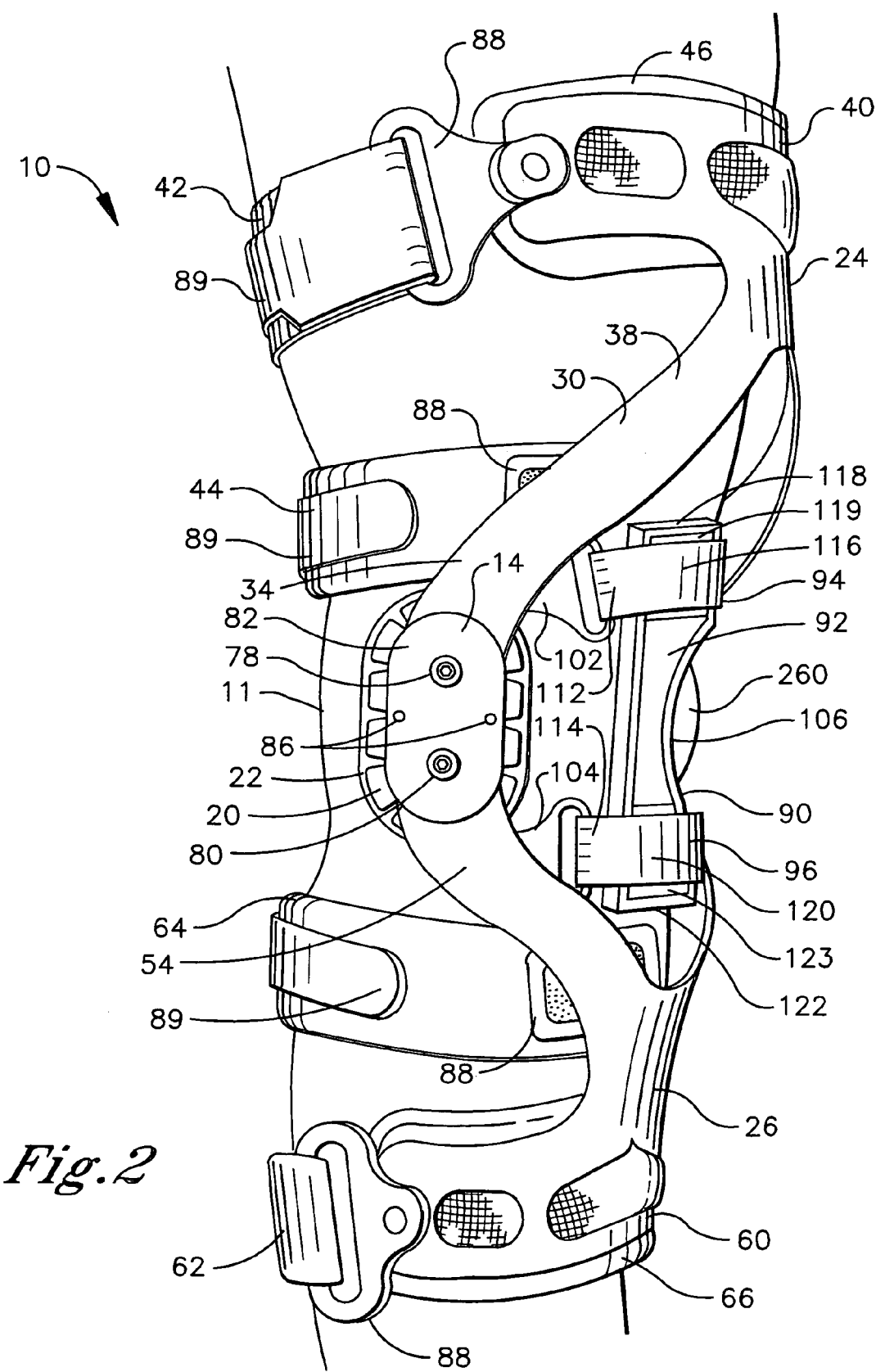
FIG. 2 is a lateral view of the knee brace of FIG. 1 operatively positioned about the knee joint of a user with the knee joint in the extension position.

Referring initially to FIGS. 1–4, a knee brace of the present invention generally designated 10 is shown operatively positioned about the knee joint 11 of a user. For purposes of illustration, the knee brace 10 is configured for mounting on the right leg, but it is understood that the skilled artisan can readily adapt the knee brace 10 for mounting on the opposite leg in accordance with the instant teaching. The positional terms "upper" and "lower" are used hereafter to define the vertical position of an element relative to the knee joint 11. The positional terms "medial" and "lateral" and "anterior" and "posterior" are used hereafter to define the horizontal position of an element relative to the vertical longitudinal axis of the body.

The knee brace 10 comprises a first hinge assembly 12 and a second hinge assembly 14. A first condyle engagement assembly comprising a first condyle cup 16 and a first condyle pad 18 is associated with the first hinge assembly 12. A second condyle engagement assembly comprising a second condyle cup 20 and a second condyle pad 22 is similarly associated with the second hinge assembly 14.

The knee brace 10 further comprises an upper brace assembly 24 and a lower brace assembly 26 opposingly positioned about the first and second hinge assemblies 12, 14. The upper brace assembly 24 includes first and second upper arms 28, 30. The first upper arm 28 has a lower end 32 rotatably coupled with the first hinge assembly 12 and the second upper arm 30 has a lower end 34 rotatably coupled with the second hinge assembly 14. The first upper arm 28 has an upper end 36 and the second upper arm 30 has an upper end 38, both of which are coupled with an upper cuff 40. The upper brace assembly 24 extends along the length of the upper leg of the user and is retained in removable engagement with the upper leg by means of first and second upper circumferential straps 42, 44. An upper pad 46 is provided to cushion the anterior of the user's upper leg from the upper cuff 40 and secure the fit of the knee brace 10 with the upper leg.

The lower brace assembly 26 includes first and second lower arms 48, 50. The first lower arm 48 has an upper end 52 rotatably coupled with the first hinge assembly 12 and the second lower arm 50 has an upper end 54 rotatably coupled with the second hinge assembly 14. The first lower arm 48 has a lower end 56 and the second lower arm 50 has a lower end 58, both of which are coupled with a lower cuff 60. The lower brace assembly 26 extends along the length of the lower leg of the user and is retained in removable engagement with the lower leg by means of first and second lower circumferential straps 62, 64. A lower pad 66 is provided to cushion the anterior of the user's lower leg from the lower cuff 60 and secure the fit of the knee brace 10 with the lower leg.

The first and second upper arms 28, 30 and upper cuff 40 are preferably integrally constructed as a unitary member. An example of first and second arms and a cuff integrally constructed as a unitary member is shown and described in U.S. Pat. No. 5,782,780, incorporated herein by reference. The first and second lower arms 48, 50 and lower cuff 60 are likewise preferably integrally constructed as a unitary member in essentially the same manner as the first and second upper arms 28, 30 and upper cuff 40. The arms 28, 30, 48, 50 and cuffs 40, 60 have semi-rigid flexibility characteristics. In particular, the arms 28, 30, 48, 50 and cuffs 40, 60 each have a relatively larger dimension of width providing substantial inflexibility in the direction of the width and have a relatively smaller dimension of thickness providing a limited degree of flexibility in the direction of the thickness. The arms 28, 30, 48, 50 and cuffs 40, 60 are preferably formed from one or more of the following types of materials which are well-known to those skilled in the art of hinged knee braces: metals, fiberglass, graphite, resins, plastics, composites and combinations thereof.

The first hinge assembly 12 is a rotational structure, which enables the knee brace 10 to track and stabilize motion of the knee joint 11 in a vertical plane. As such, the first hinge assembly 12 rotationally connects the lower end 32 of the first upper arm 12 and the upper end 22 of the first lower arm 14 about a first hinge pivot. The first hinge assembly 28 is a termed a polycentric hinge assembly because the first hinge pivot has two distally separate pivot elements 68, 70, which enable cooperative rotation of the first upper arm 28 and the first lower arm 48 about two distally separate centers of rotation. In particular, the first hinge pivot has a first upper pivot element 68 positioned at an upper center of rotation, about which the first upper arm 28 rotates, and a first lower pivot element 70 positioned at a lower center of rotation, about which the first lower arm 48 rotates. The first upper and lower pivot elements 68, 70 are conventional rivets extending through the first hinge assembly 12. Alternatively, the first upper and/or lower pivot elements are a rivet of the type disclosed in U.S. Pat. No. 5,807,294, incorporated herein by reference, which includes an adjustment member.

Cooperative rotation of the first upper arm 28 and the first lower arm 48 in unison about the first hinge pivot is enabled by a plurality of intermeshing teeth 71 (shown in FIG. 5) formed on the lower end 32 of the first upper arm 28 and the upper end 52 of the first lower arm 48, respectively. The first hinge assembly 12 is essentially rigid except for the upper and lower ends 52, 32 extending away from the first hinge assembly 12, which are semi-rigid, having a limited degree of flexibility as described above. Exemplary polycentric hinge assemblies are disclosed in above-recited U.S. Pat. No. 5,807,294 as well as U.S. Pat. No. 5,772,618, incorporated herein by reference.

The first hinge assembly 12 further comprises a first outer hinge plate 72, a first condyle plate 74, and a plurality of first hinge fasteners 76. The first outer hinge plate 72 is an oval-shaped structure forming the outside face of the first hinge assembly 12, which is distal to the user. The first outer hinge plate 72 shields the inner workings of the first hinge assembly 12 from the environment to avoid external interference during operation. The first condyle plate 74 is likewise an oval-shaped structure, which is positioned opposite the first outer hinge plate 72 more proximal to the user. The configuration of the first condyle plate 74 differs from the configuration of the first outer hinge plate 72 in a manner described in greater detail hereafter. The hinge fasteners 76 extend through the first hinge assembly 12 from the first outer hinge plate 72 to the first condyle plate 74 and cooperate with the first upper and lower pivot elements 68, 70 to maintain proper positioning of the components of the first hinge assembly 12. The hinge fasteners 76 are preferably conventional threaded screws.

The first condyle cup 16 is positioned adjacent to the first condyle plate 74 and is connected to the first hinge assembly 12 by means of fasteners, adhesives or the like. The first condyle cup 16 is formed from a stiffened material, such as a conventional plastic, which has a plurality of flexion slits formed in its periphery, as disclosed in above-recited U.S. Pat. No. 5,807,294, to enhance the flexibility thereof. The first condyle cup 16 has a concave configuration to receive the knee condyle projecting from the medial side of the knee joint 11. The first condyle pad 18 is preferably fitted in the first condyle cup 16 and attached thereto to cushion the knee condyle from the stiffened first condyle cup 16. Attachment of the first condyle pad 18 to the first condyle cup 16 is effected in an essentially permanent manner by conventional means, such as an adhesive, or in a selectively detachable manner by conventional means such as releasable hook and loop fasteners commercially available under the trade name "VELCRO". The first condyle pad 18 is a thickened continuous cushion formed from a conventional pliant padding material, such as a foam, or is alternatively a fluid-containing cushion, such as a pneumatic bladder. The first condyle cup 16 and associated first condyle pad 18 maintain the close fit of the knee brace 10 to the knee joint 11 during use. The position of the first condyle cup 16 and associated first condyle pad 18 may be adjustable relative to the knee joint 11 to more precisely fit the knee brace 10 to the user, when the first upper pivot element 68 is provided with an adjustment member and/or the first lower pivot element 70 is provided with an adjustment member as described hereafter.

The second hinge assembly 14 is a rotational structure similar to the first hinge assembly 12, which likewise enables the knee brace 10 to track and stabilize motion of the knee joint 11 in a vertical plane. As such, the second hinge assembly 14 rotationally connects the lower end 34 of the second upper arm 30 and the upper end 54 of the second lower arm 50 about a second hinge pivot. The second hinge assembly 14 is preferably a polycentric hinge assembly including a second upper pivot element 78, a second lower pivot element 80, second intermeshing teeth 81 (shown in FIG. 6), a second outer hinge plate 82, a second condyle plate 84, and second hinge fasteners 86, which are constructed and function in essentially the same manner as described above with respect to corresponding elements of the first hinge assembly 12. The second condyle cup 20 and second condyle pad 22 are constructed and function in essentially the same manner as the first condyle cup 16 and first condyle pad 18 described above.

The circumferential straps 42, 44, 62, 64 secure the knee brace 10 to the leg of a user and counterbalance rotation of the first and second hinge assemblies 12, 14. The circumferential straps 42, 44, 62, 64 are formed from a fabric which is flexible, but essentially non-stretchable. The first upper circumferential strap 42 extends posteriorly behind the upper cuff 40 and is releasably and adjustably connected to opposing sides of the upper cuff 40 by attaching opposite ends of the first circumferential strap 42 to circumferential strap connectors 88, which in turn are releasably attached to the opposing sides of the upper cuff 40. The second upper circumferential strap 44 extends posteriorly behind the first and second upper arms 28, 30 and is releasably and adjustably connected to the first and second upper arms 28, 30 in essentially the same manner as described above with respect to the first upper circumferential strap 42 and upper cuff 40. The first lower circumferential strap 62 extends posteriorly behind the lower cuff 60 and is releasably and adjustably connected to the lower cuff 60 in essentially the same manner as described above. The second lower circumferential strap 64 extends posteriorly behind the first and second lower arms 48, 50 and is releasably and adjustably connected to the first and second lower arms 48, 50 in essentially the same manner as described above.

The circumferential strap connectors 88 are preferably selected from among the connectors and/or attachment assemblies disclosed in U.S. Patent Publication Nos. 2003-0176824 and 2003-0176823, incorporated herein by reference. The lengths of the circumferential straps 42, 44, 62, 64 are adjustable by fitting the ends and mid-section of each circumferential strap with releasable cooperative releasable fasteners 89, preferably conventional "VELCRO" releasable hook and loop fasteners. The ends of the circumferential strap are doubled back over the mid-section to a selected point on the mid-section of the circumferential strap and releasably fastened to the mid-section at the selected point. Although not shown, it is further within the scope of the present invention to provide the circumferential straps 42, 44, 62, 64 with supplemental padding for the comfort of the user.

The knee brace 10 is provided with a patellar tracking assembly which enables the knee brace 10 to track and prevent patellar displacement of the knee joint 11 in a horizontal plane. The patellar tracking assembly comprises a tracking guide 90, a compression plate 92, an upper tension strap 94, a lower tension strap 96, an upper tension strap connector 98, a lower tension strap connector 100, an upper counterbalance connector 102, and a lower counterbalance connector 104. The tracking guide 90 is formed from a somewhat pliant material, such as a dense neoprene foam, and the compression plate 92 is formed from an at least somewhat less pliant material, such as a semi-rigid sheet plastic or metal. The tracking guide 90 and compression plate 92 are configured in essentially the same shape. The compression plate 92 is superposed over and fixedly attached to the tracking guide 90, thereby functioning as a stiffener for the tracking guide 90. The tracking guide 90 has an inside face 106 with an arcuate profile essentially corresponding to that of the periphery of a patella. The upper and lower tension straps 94, 96 are constructed from a fabric which is flexible, but essentially non-stretchable.

The upper and lower tension strap connectors 98, 100 and upper and lower counterbalance connectors 102, 104 are preferably the same or similar to the connectors disclosed in above-cited U.S. Patent Publication Nos. 2003-0176824. The upper and lower tension strap connectors 98, 100 provide releasable and adjustable attachment of the upper and lower tension straps 94, 96, respectively, to the first hinge assembly 12. The upper and lower counterbalance connectors 102, 104 similarly provide releasable and adjustable attachment of the upper and lower tension straps 94, 96, respectively, to the second hinge assembly 14. In particular, the upper and lower tension straps 94, 96 have ends 108, 110, which are fixably attached to the upper and lower tension strap connectors 98, 100. The upper and lower tension strap connectors 98, 100 are in turn releasably attached to the first hinge assembly 12 in a manner disclosed in U.S. Patent Publication Nos. 2003-0176824.

The upper and lower tension straps 94, 96 have opposite ends 112, 114, which are releasably and adjustably attached to the upper and lower counterbalance connectors 102, 104 by fitting the ends and mid-section of the upper and lower tension straps 94, 96 with releasable cooperative releasable fasteners 115, preferably conventional "VELCRO" releasable hook and loop fasteners. The ends 112, 114 are threaded through the upper and lower counterbalance connectors 102, 104, respectively. Each end 112, 114 is doubled back over the mid-section of the respective tension strap 94, 96 to a selected point on the mid-section and releasably fastened to the mid-section at the selected point. The upper and lower counterbalance connectors 102, 104 are in turn releasably attached to the second hinge assembly 14 in a manner disclosed in U.S. Patent Publication No. 2003-0176824.

An upper loop 116 is created in the upper tension strap 94 by doubling the end 112 back over the mid-section of the upper tension strap 94. The upper loop 116 receives an upper end 118 of the tracking guide 90 and compression plate 92. The upper tension strap 94 engages the upper end 118 and preferably is releasably attached to the upper end 118 by means of cooperative releasable fasteners 119 affixed to the upper anterior face of the compression plate 92 and integral with the face of the upper tension strap 94. The fasteners 119 are preferably conventional "VELCRO" releasable hook and loop fasteners. A lower loop 120 is similarly created in the lower tension strap 96 by doubling the end 114 back over the mid-section of the lower tension strap 96. The lower loop 120 receives a lower end 122 of the tracking guide 90 and compression plate 92. The lower tension strap 96 engages the lower end 122 and preferably is releasably attached to the lower end 122 by means of cooperative releasable fasteners 123 affixed to the lower anterior face of the compression plate 98 and integral with the face of the lower tension strap 96. The fasteners 123 are preferably conventional "VELCRO" releasable hook and loop fasteners.

Figure 5:
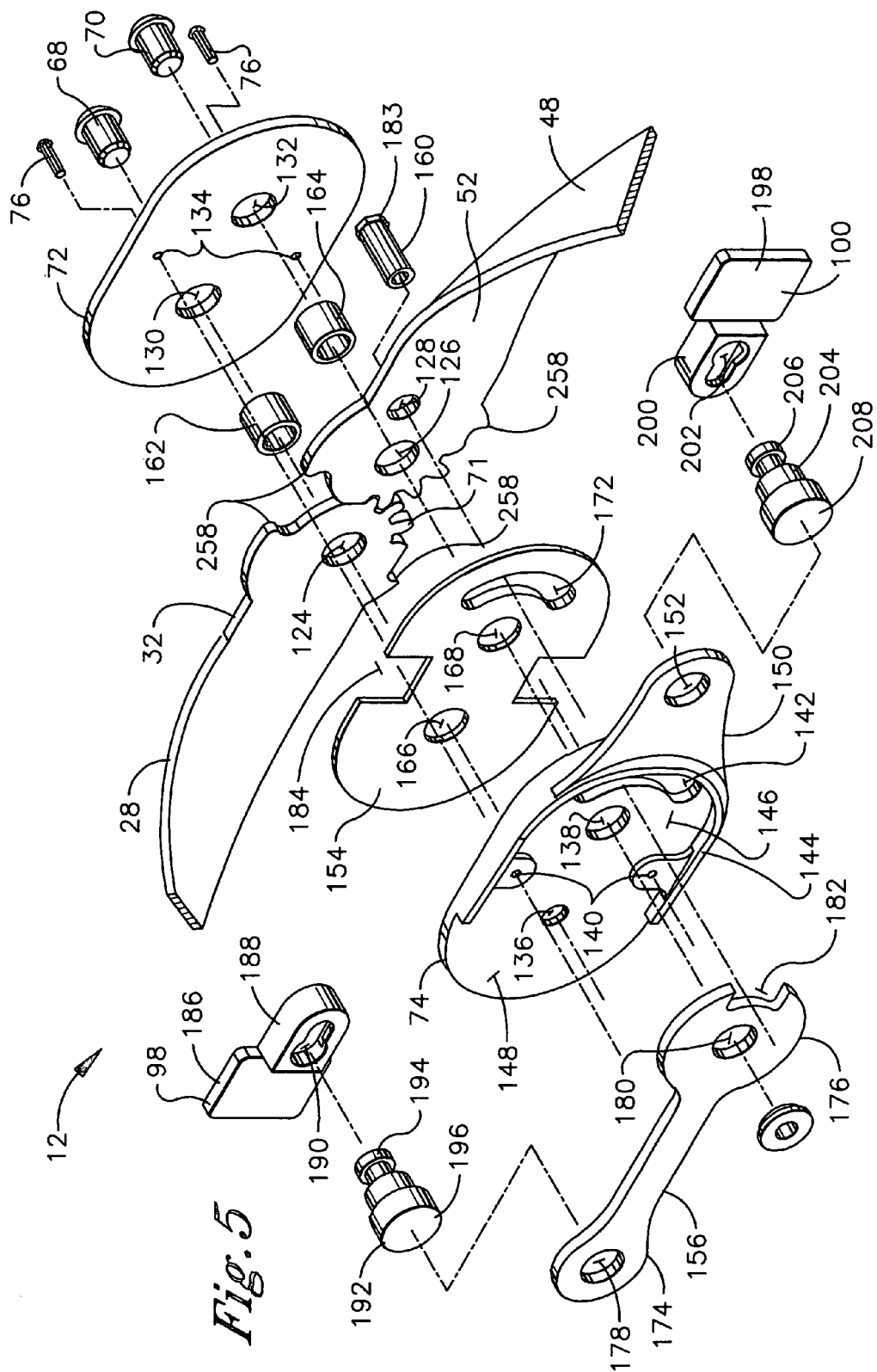
FIG. 5 is a detailed exploded perspective view of a first hinge assembly of the knee brace of FIG. 1, wherein the first hinge assembly includes dynamic elements which complement the patellar tracking function of the knee brace.

In addition to the above-recited structural elements of the first hinge assembly 12, which enable the knee brace 10 to track and stabilize motion of the knee joint 11, the first hinge assembly 12 further comprises structural elements, which dynamically function in cooperation with the patellar tracking assembly to complement the function of the knee brace 10 to track and prevent patellar displacement in a horizontal plane. Referring to FIG. 5, the first hinge assembly 12 further comprises a first upper arm pivot aperture 124 formed through the lower end 32 of the first upper arm 28 and a first lower arm pivot aperture 126 and a lower arm drive bushing aperture 128 formed through the upper end 52 of the first lower arm 48. Upper and lower first outer hinge plate pivot apertures 130, 132 and first outer hinge plate fastening apertures 134 are formed through the first outer hinge plate 72. Upper and lower first condyle plate pivot apertures 136, 138 and first condyle plate fastening apertures 140 are correspondingly formed through the first condyle plate 74. A condyle plate drive bushing slot 142 is also formed through the first condyle plate 74.

The first condyle plate 74 has a raised edge 144, which extends continuously around the lower, medial, and lateral periphery of the first condyle plate 74. The raised edge 144 forms a wall, which defines a lever rotation chamber 146 internal to the raised edge 144. The raised edge 144 terminates at the upper periphery of the first condyle plate 74 to define an upper opening 148 of the lever rotation chamber 146. The first condyle plate 74 also has a first lower tension strap mount 150 extending from its lower periphery, which is statically attached thereto and is preferably integral with the first condyle plate 74. A first lower mount anchor aperture 152 is formed through the first lower tension strap mount 150.

The first hinge assembly 12 further comprises inner workings including a first inner hinge plate 154, an upper tension strap lever 156, a drive bushing 160, an upper pivot bushing 162, and a lower pivot bushing 164. The above-recited inner workings are constructed from one or more high-strength relatively rigid materials, such as metals and the like. The first inner hinge plate 154 is an oval-shaped structure having essentially the same dimensions as the first outer hinge plate 72. Upper and lower first inner hinge plate pivot apertures 166, 168 and an inner hinge plate drive bushing slot 172 are formed through the first inner hinge plate 154.

The upper tension strap lever 156 has a tapered external end 174 and a widened internal end 176. A lever anchor aperture 178 is formed through the external end and a lever pivot aperture 180 and a drive bushing notch 182 are formed through the internal end 176. The upper tension strap lever 156 is rotationally displaceable about the first lower pivot element 70 and the lower pivot bushing 164 relative to the first outer hinge plate 72, first inner hinge plate 154, and first condyle plate 74 during operation of the first hinge assembly 12 as described below. However, the internal end 176 remains internal to the lever rotation chamber 146 of the first condyle plate 74 at all times without extending past the edges of the first outer hinge and first condyle plates 72, 74 during operation. In contrast, the external end 174 extends outside the lever rotation chamber 146 and past the edges of the first outer hinge and first condyle plates 72, 74 at all times during operation.

Although it is apparent to the skilled artisan that the invention is not limited to any one specific sequential order of components within the first hinge assembly 12, a preferred sequence of components is shown herein, which proceeds proximally in the direction of the knee joint 11 as follows: the first outer hinge plate 72, the lower and upper ends 32, 52 of the first upper and lower arms 28, 48, respectively, the first inner hinge plate 154, the first condyle plate 74, and the upper tension strap lever 156.

The first outer hinge plate 72, lower end 32, first inner hinge plate 154, and first condyle plate 74 are oriented relative to each other such that the upper first outer hinge plate pivot aperture 130, first upper arm pivot aperture 124, upper first inner hinge plate pivot aperture 166, and upper first condyle plate pivot aperture 136 are all in alignment with one another to receive the first upper pivot element 68 therethrough. The diameter of the upper pivot bushing 162 is correspondingly sized such that the upper pivot bushing 162 is relatively closely fitted within the upper first outer hinge plate pivot aperture 130, first upper arm pivot aperture 124, and upper first inner hinge plate pivot aperture 166. Accordingly, the first upper arm 28 is rotationally displaceable about the first upper arm pivot aperture 124, upper pivot bushing 162 and first upper pivot element 68 relative to the first outer hinge plate 72, first inner hinge plate 154, and first condyle plate 74.

The first outer hinge plate 72, upper end 52, first inner hinge plate 154, upper tension strap lever 156, and first condyle plate 74 are likewise oriented such that the lower first outer hinge plate pivot aperture 132, first lower arm pivot aperture 126, lower first inner hinge plate pivot aperture 168, first lower condyle plate pivot aperture 138, and lever pivot aperture 180 are all in alignment with one another to receive the first lower pivot element 70. Accordingly, the upper tension strap lever 156 is rotationally displaceable about the first lower pivot aperture 180 and first lower pivot element 70 relative to the first outer hinge plate 72, first inner hinge plate 154, and first condyle plate 76, subject to rotation limitations imposed by the drive bushing 160 described below.

The diameter of the lower pivot bushing 164 is correspondingly sized such that the lower pivot bushing 164 is relatively closely fitted within the lower first outer hinge plate pivot aperture 132, first lower arm pivot aperture 126, and first lower inner hinge plate pivot aperture 168. Accordingly, the first lower arm 48 is rotationally displaceable about the first lower arm pivot aperture 126, lower pivot bushing 164 and first lower pivot element 70 relative to the first outer hinge plate 72, first inner hinge plate 154, and first condyle plate 76.

The upper end 52 of the first lower arm 48, first inner hinge plate 154, first condyle plate 74, and upper tension strap lever 156 are oriented such that the lower arm drive bushing aperture 128, inner hinge plate drive bushing slot 172, condyle plate drive bushing slot 142, and drive bushing notch 182 are all in alignment with one another to receive the drive bushing 160 therethrough. The drive bushing 160 is a cylindrical member sized in relatively close fitting relationship with the lower arm drive bushing aperture 128.

The drive bushing 160 has a widened head 183, which clears or slidably engages the inside face of the first outer hinge plate 72 to retain the drive bushing 160 within the lower arm drive bushing aperture 128. Accordingly, rotational displacement of the first lower arm 48 effects rotational displacement of the drive bushing 160.

The inner hinge plate drive bushing slot 172 and condyle plate drive bushing slot 142 are sized substantially larger than the lower arm drive bushing aperture 128, which enables the drive bushing 160 to travel freely within the inner hinge plate drive bushing slot 172 and condyle plate drive bushing slot 142 without engaging the ends of either slot 172, 142 when the first lower arm 48 is rotationally displaced within its normal operational limits of rotation. Accordingly, rotational displacement of the drive bushing 160 does not effect displacement of the first outer hinge plate 72, first inner hinge plate 154, or first condyle plate 74. The drive bushing notch 182 is sized such that the drive bushing 160 is rotationally displaced into engagement with at least one end of the drive bushing notch 182 as the first lower arm 48 rotationally approaches its normal operational limits of rotation. Accordingly, rotational displacement of the drive bushing 160 effects rotational displacement of the upper tension strap lever 156 about the lever pivot aperture 180 and the first lower pivot element 70.

The first outer hinge plate 72, first inner hinge plate 154, and first condyle plate 74 are oriented such that the first outer hinge plate fastening apertures 134 and first condyle plate fastening apertures 140 are in alignment with one another to receive the first hinge fasteners 76 therethrough. First inner hinge plate clearance notches 184 are provided in the edge of the first inner hinge plate 154, which enable the first hinge fasteners 76 to extend from the first outer hinge plate 72 to first condyle plate without engaging the first inner hinge plate 154. The diameter of the first hinge fasteners 76 are sized such that the first hinge fasteners 76 are closely fitted within the first outer hinge plate fastening apertures 134 and first condyle plate fastening apertures 140 to maintain the position of the first outer hinge plate 72, inner hinge plate 108, and first condyle plate 74 fixed relative to one another.

As noted above, the upper and lower tension strap connectors 98, 100 each have essentially the same construction and enable releasable connection of the upper and lower tension straps 94, 96, respectively, to the first hinge assembly 12. The upper tension strap connector 98 has an upper tension strap attachment portion 186 and a lever attachment portion 188 at opposite ends. The upper tension strap attachment portion 186 is a thin flat tab to which the end 108 of the upper tension strap 94 is substantially permanently attached by means such as sewing, adhesion, or the like. The lever attachment portion 188 is a body having an upper receptacle 190, which is configured to selectively releasably and rotationally retain a first upper anchor 192. In particular, the first upper anchor 192 has a narrower upper retention portion 194 sized to fit within the upper receptacle 190 and to be releasably retained therein. The first upper anchor 192 also has a widened upper base portion 196 correspondingly sized to closely fit within the lever anchor aperture 178 and to be substantially permanently retained therein.

The upper tension strap connector 98 effects releasable connection of the upper tension strap 94 to the first hinge assembly 12 by means of permanent attachment between the upper tension strap attachment portion 186 and the end 108 of the upper tension strap 94, releasable attachment between the upper receptacle 190 and the upper retention portion 194, and permanent attachment between the lever anchor aperture 178 and the upper base portion 196. As such, the first upper anchor 192 functions as a connection point between the upper tension strap 94 and the first hinge assembly 12.

The lower tension strap connector 100 correspondingly has a lower tension strap attachment portion 198 and a first lower mount attachment portion 200 at opposite ends. The lower tension strap attachment portion 198 is substantially permanently attached to the end 110 of the lower tension strap 96 and the first lower mount attachment portion 200 has a lower receptacle 202 configured to selectively releasably and rotationally retain a first lower anchor 204. In particular, the first lower anchor 204 has a narrower lower retention portion 206 sized to fit within the lower receptacle 202 and to be releasably retained therein. The first lower anchor 204 also has a widened lower base portion 208 correspondingly sized to closely fit within the first lower mount anchor aperture 152 and to be substantially permanently retained therein. Accordingly, the lower tension strap connector 100 effects releasable connection of the lower tension strap 96 to the first hinge assembly 12 by means of permanent attachment between the lower tension strap attachment portion 98 and the end 110 of the lower tension strap 96, releasable attachment between the lower receptacle 202 and the lower retention portion 206, and permanent attachment between the first lower mount anchor aperture 152 and the lower base portion 208. As such, the first lower anchor 204 functions as a connection point between the lower tension strap 96 and the first hinge assembly 12.

Although not shown, it is within the scope of the present invention and readily within the purview of the skilled artisan to alternately construct the first hinge assembly 12 so that the widened internal end 176 of the upper tension strap lever 156 is connected to and rotatable about an alternate pivot element other than the first lower pivot element 70, wherein the alternate pivot element still enables the upper tension strap lever 156 to rotate about the first hinge pivot as shown and described herein. For example, the alternate pivot element, about which the widened internal end 176 is rotatable and to which the widened internal end 176 is connected, can be the first upper pivot element 68 or a pivot element dedicated to the upper tension strap lever 156 independent of the first upper and lower pivot elements 68, 70. It is apparent to the skilled artisan that the term "first hinge pivot" is used herein to encompass any structure or structures included within or proximal to the first hinge assembly 12, about which the upper tension strap lever 156, the first upper arm 28 or the first lower arm 48 is rotatable.

Figure 6:
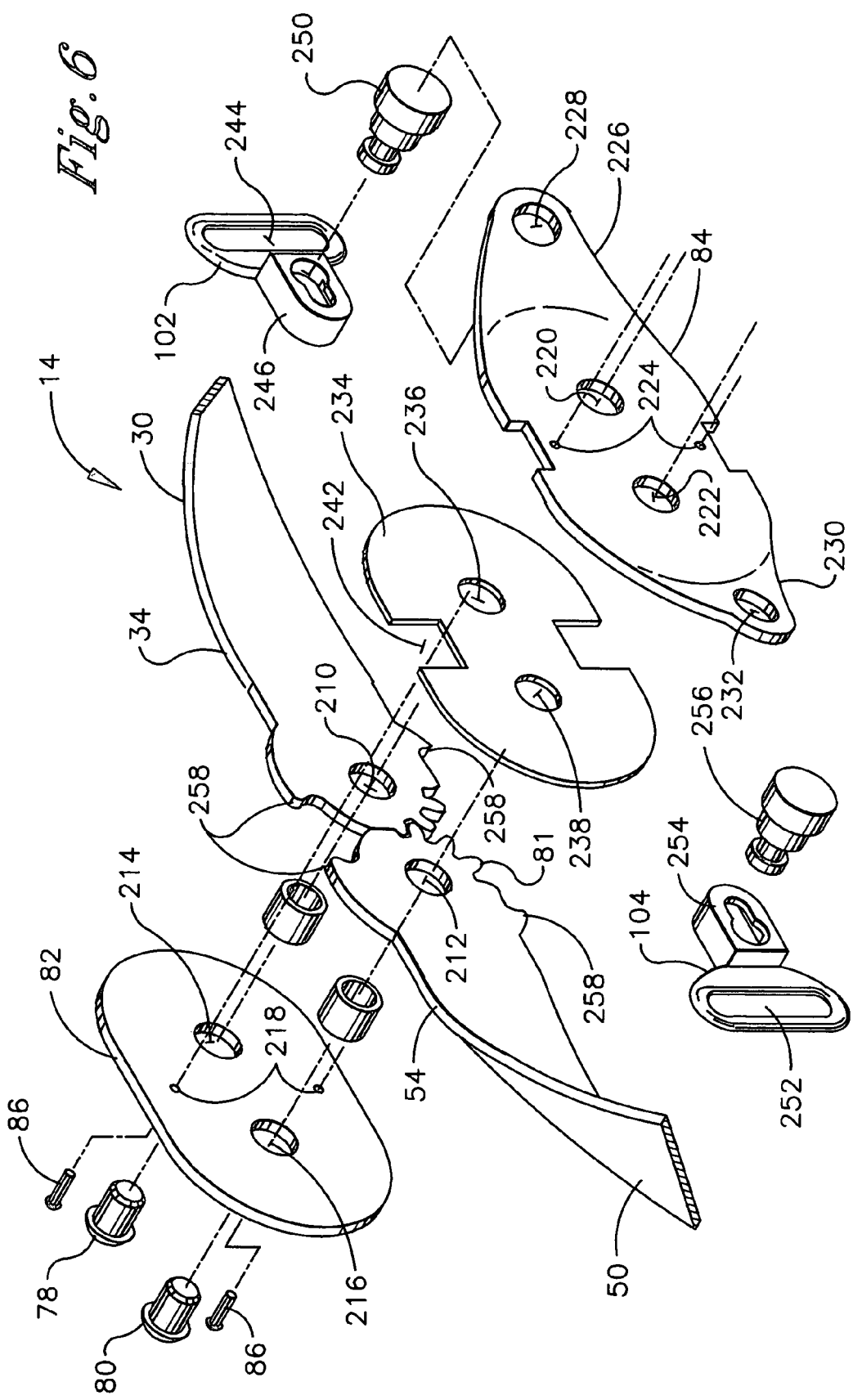
FIG. 6 is a detailed exploded perspective view of a second hinge assembly of the knee brace of FIG. 1, wherein the second hinge assembly includes static elements which complement the patellar tracking function of the knee brace.

In addition to the above-recited structural elements of the second hinge assembly 14, which enable the knee brace 10 to track and stabilize motion of the knee joint 11, the second hinge assembly 14 further comprises structural elements, which dynamically function in cooperation with the patellar tracking assembly to complement the function of the knee brace 10 to track and prevent patellar displacement in a horizontal plane. Referring to FIG. 6, the second hinge assembly 14 further comprises a second upper arm pivot aperture 210 formed through the lower end 34 of the second upper arm 30 and a second lower arm pivot aperture 212 formed through the upper end 54 of the second lower arm 50. Upper and lower second outer hinge plate pivot apertures 214, 216 and second outer hinge plate fastening apertures 218 are formed through the second outer hinge plate 82. Upper and lower second condyle plate pivot apertures 220, 222 and second condyle plate fastening apertures 224 are correspondingly formed through the second condyle plate 84.

The second condyle plate 84 has an upper tension strap mount 226 extending from its upper periphery and statically attached to the second condyle plate 84, preferably integral therewith. An upper mount anchor aperture 228 is formed through the upper tension strap mount 226. The second condyle plate 84 also has a second lower tension strap mount 230 extending from its lower periphery and statically attached to the second condyle plate 84, preferably integral therewith. A second lower mount anchor aperture 232 is formed through the second lower tension strap mount 230.

The second hinge assembly 14 further comprises a second inner hinge plate 234. The second inner hinge plate 234 is an oval-shaped structure having essentially the same dimensions as the second outer hinge plate 82. Upper and lower second inner hinge plate pivot apertures 236, 238 are formed through the second inner hinge plate 234. The second outer hinge plate 82, lower end 34, second inner hinge plate 234, and second condyle plate 84 are oriented relative to each other such that the upper second outer hinge plate pivot aperture 236, second upper arm pivot aperture 210, upper second inner hinge plate pivot aperture 236, and second upper condyle plate pivot aperture 220 are all in alignment with one another to receive the second upper pivot element 78 therethrough. Accordingly, the second upper arm 30 is rotationally displaceable about the second upper arm pivot aperture 210 and second upper pivot element 78 relative to the second outer hinge plate 82, second inner hinge plate 234, and second condyle plate 84.

The second outer hinge plate 82, upper end 54, second inner hinge plate 234, and second condyle plate 84 are likewise oriented such that the lower second outer hinge plate pivot aperture 216, second lower arm pivot aperture 212, lower second inner hinge plate pivot aperture 238, and lower second condyle plate pivot aperture 222 are all in alignment with one another to receive the second lower pivot element 80. Accordingly, the second lower arm 50 is rotationally displaceable about the second lower arm pivot aperture 212 and second lower pivot element 80 relative to the second outer hinge plate 82, second inner hinge plate 234, and second condyle plate 84.

The second outer hinge plate 82, second inner hinge plate 234, and second condyle plate 84 are oriented such that the second outer hinge plate fastening apertures 218 and second condyle plate fastening apertures 224 are in alignment with one another to receive the second hinge fasteners 86 therethrough. Second inner hinge plate clearance notches 242 are provided in the edge of the second inner hinge plate 234, which enable the second hinge fasteners 86 to extend from the second outer hinge plate 82 to the second condyle plate 84 without engaging the second inner hinge plate 234. The diameter of the second hinge fasteners 86 are sized such that the second hinge fasteners 86 are closely fitted within the second outer hinge plate fastening apertures 218 and second condyle plate fastening apertures 224 to maintain the position of the second outer hinge plate 82, second inner hinge plate 234, and second condyle plate 84 fixed relative to one another.

The upper and lower counterbalance connectors 102, 104 each have essentially the same construction to enable releasable connection of the upper and lower tension straps 94, 96, respectively, to the second hinge assembly 14. In particular, the upper counterbalance connector 102 has an upper tension strap attachment loop 244, through which the end 112 of the upper tension strap 94 is threaded. The upper counterbalance connector 102 also has an upper mount attachment portion 246, which is essentially identical to the lever attachment portion 188 or first lower mount attachment portion 200 of FIG. 5. The upper mount attachment portion 246 releasably attaches to a second upper anchor 250 permanently retained in the upper mount anchor aperture 228. The lower counterbalance connector 104 has a lower tension strap attachment loop 252, through which the end 114 of the lower tension strap 96 is threaded. The lower counterbalance connector 104 also has a lower mount attachment portion 254, which releasably attaches to a second lower anchor 256 permanently retained in the second lower mount anchor aperture 232.

Although a preferred embodiment of the upper and lower counterbalance connectors is described above and shown in the drawing, it is understood that the present invention is not limited to a specific embodiment of the counterbalance connectors. The present invention encompasses counterbalance connectors having alternate connective structures or locations of connection within the purview of the skilled artisan which maintain a static counter force on the tracking guide 90 and compression plate 92 in a direction opposite the first hinge assembly 12 and opposing the tension force of the upper and lower tension straps 94, 96 described hereafter.

The first upper and lower arms 28, 48 of the first hinge assembly 12 and/or the second upper and lower arms 30, 50 of the second hinge assembly 14 may additionally be provided with fixed rotation stops 258 shown in FIGS. 5 and 6 or adjustable rotation stops (not shown), which cooperate with additional stop elements (not shown) attached to the first hinge assembly 12 and/or the second hinge assembly 14 in a conventional manner, to substantially prevent rotation of the knee brace past fixed or adjustably selected extension or flexion positions of rotation. Although the full extension position of the knee brace 10, as shown in FIGS. 1–4, is at a rotation angle of 180°, in practice the fixed rotation stops 258 preferably cooperate with additional stop elements attached to the first or second hinge assembly 12, 14 to substantially prevent rotation of the knee brace 10 past a rotation angle of about 170°. As a result, the knee joint 11 is not permitted to extend past about the final 10° of extension, thereby reducing the risk hyperextension of the knee joint 11 when the knee brace 10 is operational as described hereafter.

Operation of the knee brace 10 is described with continuing reference to FIGS. 1–6 and further reference to FIGS. 7–9. The knee brace 10 is positioned on the knee joint 11 for which patellar stabilization is desired by placing the upper and lower cuffs 40, 60 on the right leg of a user with the first and second condyle pads 18, 22 appropriately positioned against the condyles of the knee joint 11. The user manually positions the tracking guide 90 at the lateral side of the femoral head adjacent to the patella 260 and trochlea behind the patella 260, taking care to insure that the tracking guide 80 does not overlap the patella 260. The user tightens the circumferential straps 42, 44, 62, 64 in a desired sequence while the knee joint 11 is in substantially full extension. The user then flexes the knee joint 11 at an angle of about 45° from full extension while maintaining the position of the tracking guide 90 at the lateral side of the femoral head and tightens the upper and lower tension straps 94, 96 at a selected strap length which exerts a desired tension force on the compression plate 92 and tracking guide 90. The strap length is preferably maintained fixed during range of motion movement of the knee joint 11, but can be readjusted if needed by interrupting the range of motion movement and tightening or loosening the upper or lower tension straps 94, 96 to a desired degree while the knee brace 10 remains in place on the knee joint 11.

When the user performs range of motion movement on the knee joint 11, the knee brace 10 remediates existing patello-femoral joint disorders or precludes potential disorders by maintaining accurate patellar tracking of the trochlear groove to substantially prevent patellar subluxation or dislocation. Specifically, the upper and lower tension straps 94, 96 apply a tension force to the compression plate 92, which responds to the tension force by exerting a posteriorly-directed force against the tracking guide 90. Accordingly, the tension force presses and retains the tracking guide 90 in a self-adjusting position against the lateral side of the femoral head with the face of the tracking guide 90 adjoining, but not overlapping, the adjacent edge of the patella 260. The position of the tracking guide 90 enforces a desired patellar track by maintaining the patella 260 in the underlying trochlear groove and preventing the patella 260 from migrating in a lateral direction out of the trochlear groove when the knee joint 11 moves through its normal range of motion. By not overlapping the patella 260, the tracking guide 90 also substantially avoids radial compression of the patella 260 which would undesirably tend to inhibit normal range of motion of the knee joint 11 and cause pain to the user.

An advantageous feature of the knee brace 10 is the ability to self-adjust in response to changes in the position of the knee joint 11. In particular, the position of the tracking guide 90 relative to the knee joint 11 and the tension force which presses the tracking guide 90 against the femoral head are automatically self-adjusting as a function of the degree of flexion or extension of the knee joint 11. When the knee joint 11 approaches a position of full flexion, the tracking guide 90 is displaced away from the knee joint 11 and the force of the tracking guide 90 against the femoral head diminishes. However, when the knee joint 11 approaches a position of full extension, the tracking guide 90 is displaced toward the knee joint 11 and the force of the tracking guide 90 against the femoral head increases. Accordingly, the tracking guide 90 is more securely retained against the femoral head relatively proximal to the knee joint 11 when the risk of patellar subluxation or dislocation is greater, i.e., generally during the last 15° to 30° of knee extension, and less securely retained against the femoral head relatively distal from the knee joint 11 when the risk of patellar subluxation or dislocation is least, i.e., during substantial knee flexion.

Figure 3:
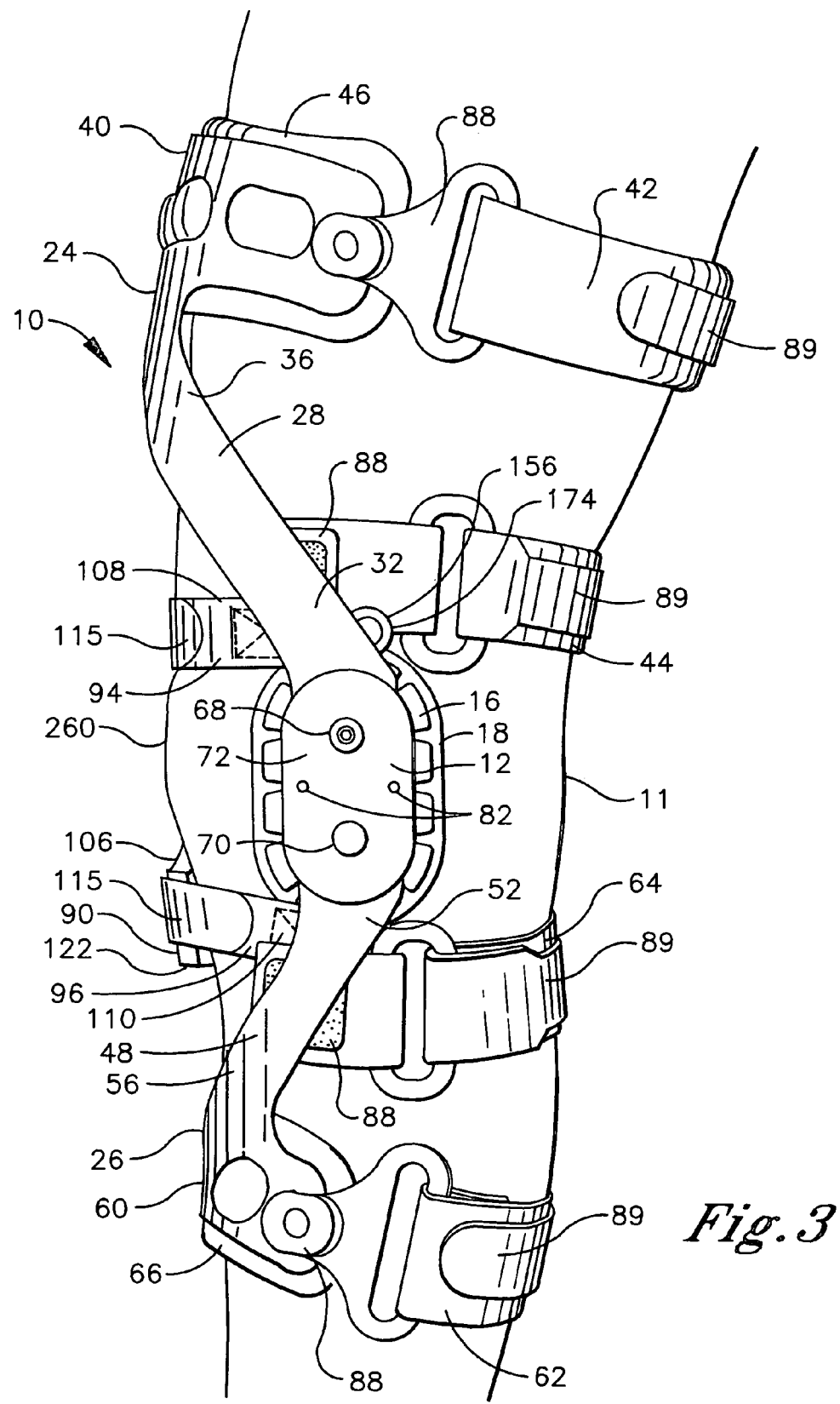
FIG. 3 is a medial view-of the knee brace of FIG. 1 operatively positioned about the knee joint of a user with the knee joint in the extension position.
Figure 4:
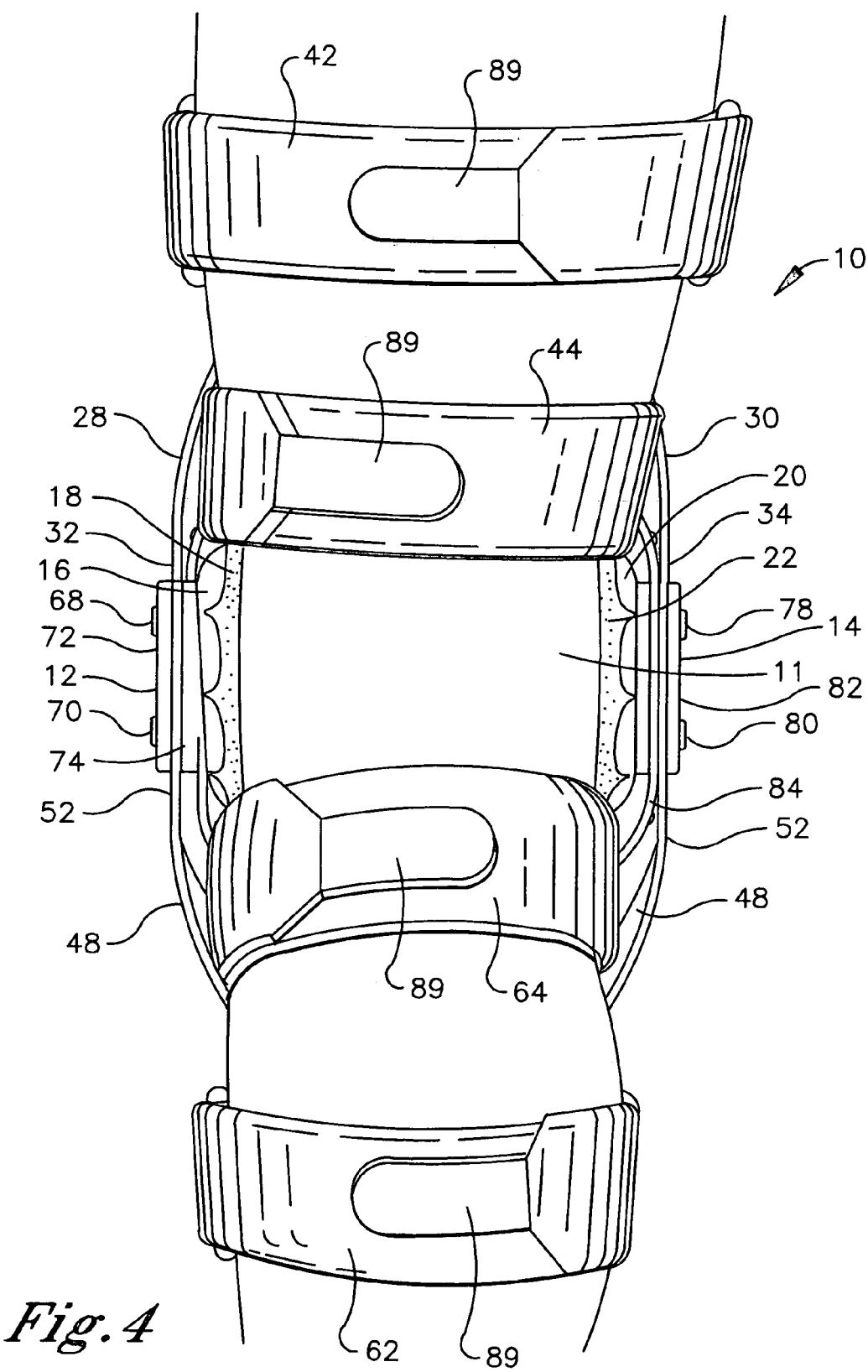
FIG. 4 is a posterior view of the knee brace of FIG. 1 operatively positioned about the knee joint of a user with the knee joint in the extension position.

The self-adjusting position and compression features of the knee brace 10 are illustrated with reference to FIGS. 3 and 7–9. Referring initially to FIG. 3, the knee brace 10 is mounted on the leg about the knee joint 11 with the knee brace 10 and the knee joint 11 in corresponding positions of substantially full extension. As such, the alignment angle β of the upper brace assembly 24 and the lower brace assembly 26 at substantially full extension is shown as approximately 180° for purposes of illustration. In practice, the alignment angle β at substantially full extension may encompass angles less than 180° to about 170° since it is often desirable to limit full extension of the knee joint 11 to somewhat less than 180° for treatment purposes as noted above.

When the knee brace 10 is in full extension, the first upper anchor 192 is aligned to one side of the first upper and lover pivot elements 68, 70 and the first upper anchor 192 is positioned relatively distal to the knee joint 11. Consequently, the upper tension strap 94 becomes more taut and the tension force which the upper tension strap 94 exerts on the compression plate 92 and tracking guide 90 increases.

Details of the inner workings of the first hinge assembly 12 when the first hinge assembly 12 is at full extension are described below with additional reference to FIG. 7, wherein the first outer hinge plate 72 and the first inner hinge plate 154 are omitted for clarity of illustration. As noted above, however, the positions of the first outer hinge plate 72, first inner hinge plate 154, and first condyle plate 74 are fixed relative to one another at all times during operation of the first hinge assembly 12. As such, the first outer hinge plate 72, the first inner hinge plate 154, and the first condyle plate 74 as well as the associated first lower tension strap mount 150 are termed static components. In contrast, the upper and lower brace assemblies 24, 26 and the upper tension strap lever 156 and associated first upper anchor 192 are termed dynamic components insofar as the positions of the upper and lower brace assemblies 24, 26 and the upper tension strap lever 156 as well as the associated first upper anchor 192 vary during operation of the first hinge assembly 12 relative to the fixed position of the first condyle plate 74, first outer hinge plate 72, and first inner hinge plate 154.

Placement of the upper and lower brace assemblies 24, 26 in the extension position, effects a series of events within the first hinge assembly 12, which cause distal positioning of the first upper anchor 192 relative to the knee joint 11. In particular, placement of the upper and lower brace assemblies 24, 26 in the extension position determines the position of the drive bushing 160 because the drive bushing 160 is retained in the lower arm drive bushing aperture 128 of the upper end 52 of the lower arm 48. The position of the drive bushing 160 correspondingly determines the position of the upper tension strap lever 156 and associated first upper anchor 192 because the drive bushing 160 is retained in the drive bushing notch 182 of the upper tension strap lever 156.

Transition of the knee brace 10 and knee joint 11 to positions of flexion is effected by rotational displacement of the knee brace 10 and the knee joint 11 away from the positions of substantially full extension shown in FIG. 3. As such, the alignment angle β of the upper brace assembly 24 and the lower brace assembly 26 is decreased from about 180° to about 90°. Rotation of the knee brace 10 to flexion anteriorly displaces the first upper anchor 192 relative to the first upper and lower pivot elements 68, 70, while posteriorly displacing the upper end 36 of the first upper arm 28 and the lower end 56 of the first lower arm 48. Accordingly, when the knee brace 10 is in flexion, the first upper anchor 192 extends anteriorly away from the first upper and lower pivot elements 68, 70 and is aligned on the opposite side of the first upper and lower pivot elements 68, 70 as compared to when the knee brace 10 is in extension. Consequently, the upper tension strap 94 becomes more slack decreasing, the tension force the upper tension strap 94 exerts on the compression plate 92 and tracking guide 90.

Details of the inner workings of the first hinge assembly 12 when the first hinge assembly 12 is at flexion are described below with reference to FIG. 8, wherein the first outer hinge plate 72 and the inner hinge plate 154 are omitted for clarity of illustration. Placement of the upper and lower brace assemblies 24, 26 in the flexion position, effects a series of events within the first hinge assembly 12, which cause proximal positioning of the first upper anchor 192 relative to the knee joint 11. In particular, placement of the upper and lower brace assemblies 24, 26 in the flexion position posteriorly displaces the drive bushing 160 in correspondence with posterior rotational displacement of the lower and upper ends 32, 52 of the first upper and lower arms 28, 48, respectively. Posterior displacement of the drive bushing 160 correspondingly posteriorly rotationally displaces the internal end 176 of the upper tension strap lever 156 and correspondingly anteriorly rotationally displaces the external end 178 of the upper tension strap lever 156 which has the first upper anchor 192 mounted thereon.

When the first hinge assembly 12 is transitioned from flexion back to extension, the above-recited series of events are reversed. In particular, return of the upper and lower brace assemblies 24, 26 to the extension position anteriorly displaces the drive bushing 160 in correspondence with anterior rotational displacement of the lower and upper ends 32, 52 of the upper and lower arms 28, 48, respectively. Anterior displacement of the drive bushing 160 correspondingly anteriorly displaces the internal end 176 of the upper tension strap lever 156 and correspondingly posteriorly rotationally displaces the external end 174 which has the first upper anchor 192 mounted thereon.

While the forgoing preferred embodiments of the invention have been described and shown, it is understood that alternatives and modifications, such as those suggested and others, may be made thereto and fall within the scope of the invention.

We claim:

1. A brace mountable about a knee having a patella to maintain proper tracking of the patella during movement of the knee, said brace comprising:
    an upper arm and a lower arm positionable about the knee;
    a hinge assembly positioned between said upper arm and said lower arm and positionable at the knee to one side of the patella, said hinge assembly having an upper pivot element, a lower pivot element, an upper tension strap lever including an upper tension strap connection point, and a lower tension strap connection point, wherein said upper arm is rotatable about said upper pivot element and said lower arm and said upper tension strap lever are rotatable about said lower pivot element to transition between a flexion position and an extension position;
    an upper tension strap connected to said upper tension strap lever at said upper tension strap connection point;
    a lower tension strap connected to said hinge assembly at said lower tension strap connection point;
    a compression member positionable on the opposite side of the patella from said hinge assembly, said upper and lower tension straps engaging said compression member to apply a tension force to said compression member, wherein said tension force increases when said upper tension strap lever rotationally transitions from said flexion position to said extension position and said tension force decreases when said upper tension strap lever rotationally transitions from said extension position to said flexion position; and
    means for applying a counter force to said compression member opposing said tension force.

2. The brace of claim 1 wherein said hinge assembly further comprises an upper tension strap connector connecting said upper tension strap to said upper tension strap connection point of said upper tension strap lever.

3. The brace of claim 1 wherein said hinge assembly further comprises a lower tension strap connector connecting said lower tension strap to said lower tension strap connection point.

4. The brace of claim 1 wherein said compression member comprises a tracking guide engaging the knee.

5. The brace of claim 1 wherein said upper arm is a first upper arm, said lower arm is a first lower arm and said hinge assembly is a first hinge assembly, said brace further comprising a second upper arm and a second lower arm and a second hinge assembly positioned between said second upper arm and said second lower arm and positionable at the knee to the opposite side of the patella from said first hinge assembly.

6. The brace of claim 5 wherein said counter force applying means is said upper tension strap extending between said compression member and said second hinge assembly.

7. An brace mountable about a knee having a patella to maintain proper tracking of the patella during movement of the knee, said brace comprising:
   an upper arm and a lower arm positionable about the knee;
   a hinge assembly positioned between said upper arm and said lower arm and positionable at the knee to one side of the patella, said hinge assembly having a hinge pivot and a tension strap lever including a tension strap connection point, wherein said upper arm, said lower arm and said tension strap lever are each rotatable about said hinge pivot to transition between a flexion position and an extension position;
   a tension strap connected to said tension strap lever at said tension strap connection point;
   a compression member positionable on the opposite side of the patella from said hinge assembly, said tension strap engaging said compression member to apply a tension force to said compression member, wherein said tension strap connection point is posteriorly displaced more distal from the patella when said tension strap lever rotationally transitions from said flexion position to said extension position and said tension strap connection point is anteriorly displaced more proximal to the patella when said tension strap lever rotationally transitions from said extension position to said flexion position; and
   means for applying a counter force to said compression member opposing said tension force.

8. A brace mountable about a knee having a patella to maintain proper tracking of the patella during movement of the knee, said brace comprising:
   an upper arm and a lower arm positionable about the knee;
   a hinge assembly positioned between said upper arm and said lower arm and positionable at the knee to one side of the patella, said hinge assembly comprising,
      a lower end of said upper arm,
      an upper end of said lower arm,
      an upper pivot element,
      a lower pivot element,
      a tension strap lever including a tension strap connection point, wherein said lower end of said upper arm is rotatable about said upper pivot element, said upper end of said lower arm is rotatable about said lower pivot element, and said tension strap lever is rotatable about said upper or lower pivot element in a first direction or a second direction, and
      a drive bushing connecting said upper or said lower arm with said tension strap lever, wherein said drive bushing displaces said tension strap lever in response to rotation of said upper and lower arms;
   a tension strap connected to said tension strap lever at said tension strap connection point;
   a compression member positionable on the opposite side of the patella from said hinge assembly, said tension strap engaging said compression member to apply a tension force to said compression member, wherein said tension force increases when said first direction is anterior and said second direction is posterior and said tension force decreases when said first direction is posterior and said second direction is anterior; and
   means for applying a counter force to said compression member opposing said tension force.

9. A method for maintaining proper patellar tracking during range of motion movement of a knee comprising:
   positioning a compression member to a first side of a patella of a knee, wherein said compression member is aligned with a desired dynamic patellar track;
   positioning a hinge assembly at said knee to a second side of said patella essentially opposite said first side, said hinge assembly providing rotation between an upper arm and a lower arm and said hinge assembly having a hinge pivot and a tension strap lever including a tension strap connection point, wherein said upper arm, said lower arm and said tension strap lever are each rotatable about said hinge pivot to transition between a flexion position and an extension position;
   engaging a tension strap with said compression member and said tension strap lever at said tension strap connection point;
   performing a range of motion movement on said knee by moving said knee from said flexion position to said extension position or from said extension position to said flexion position;
   posteriorly displacing said tension strap connection point away from said patella to tighten said tension strap and increase said tension force when said knee approaches said extension position; and
   anteriorly displacing said tension strap connection point toward said patella to slacken said tension strap and decrease said tension force when said knee approaches said flexion position.

* * * * *